United States Patent [19]

Graham et al.

[11] Patent Number: 4,725,626

[45] Date of Patent: Feb. 16, 1988

[54] MANUFACTURE OF ALCOHOLS FROM SYNTHESIS GAS

[75] Inventors: Anne M. Graham, Northfield; Thomas G. Attig, Aurora, both of Ohio

[73] Assignee: The Standard Oil Company, Cleveland, Ohio

[21] Appl. No.: 762,221

[22] Filed: Aug. 5, 1985

[51] Int. Cl.$^4$ .............................................. C07C 27/06
[52] U.S. Cl. ..................................... 518/713; 502/313
[58] Field of Search ............................................ 518/713

[56] References Cited

U.S. PATENT DOCUMENTS

| | | | |
|---|---|---|---|
| 1,859,244 | 5/1932 | Patart . | |
| 2,476,788 | 7/1949 | White | 260/450 |
| 2,535,060 | 12/1950 | Gresham | 260/448 |
| 2,542,454 | 2/1951 | Arnold et al. | 260/459 |
| 2,549,470 | 4/1951 | Hawk | 260/449 |
| 2,569,380 | 9/1951 | Holder | 260/449.5 |
| 2,753,366 | 7/1956 | Pistor | 260/449 |
| 2,787,628 | 4/1957 | Himmler et al. | 260/449 |
| 3,952,039 | 4/1976 | Walker et al. | 260/449 |
| 4,014,913 | 3/1977 | Ellgen et al. | 260/449 |
| 4,096,164 | 6/1978 | Ellgen et al. | 260/449 |
| 4,119,656 | 10/1978 | Poutsma et al. | 260/449 |
| 4,122,110 | 10/1978 | Sugier et al. | 260/449.5 |
| 4,151,192 | 4/1979 | Kaplan | 260/449 |
| 4,162,261 | 7/1979 | Kaplan | 260/449 |
| 4,162,262 | 7/1979 | Ellgen et al. | 260/449 |
| 4,211,719 | 7/1980 | Walker et al. | 260/449 |
| 4,298,354 | 11/1981 | Hardman et al. | 518/713 |
| 4,377,643 | 3/1983 | Pesa et al. | 518/713 |
| 4,476,247 | 10/1984 | Pesa et al. | 502/325 |
| 4,478,955 | 10/1984 | Pesa et al. | 518/713 |

FOREIGN PATENT DOCUMENTS 653834  5/1951  United Kingdom .
682826  11/1952  United Kingdom .

OTHER PUBLICATIONS

Inoue et al., "Alcohol Synthesis from Syngas on Ruthenium-Based Composite Catalysts", Applied Catalysis, vol. 11 (1984), pp. 103–116.

Inoue et al., "Ruthenium-Based Catalyst for the Gas-Phase Synthesis of Alcohols from CO and H2", Journal of Chemical Society, Chem. Comm (1983), pp. 70–72.

Chemical Absracts Nos. 49–4267c; 50–11935a; 57–5339h; 65–13524c; 89–62210q; and 89–16604-8j-recovery of alcohols from synthesis gas.

Primary Examiner—Howard T. Mars
Attorney, Agent, or Firm—M. F. Esposito; J. E. Miller; L. W. Evans

[57] ABSTRACT

A catalyst and process useful for the production of alcohols from CO and $H_2$. The catalyst has the formula:

$$RuCu_aM_bA_cN_zO_x$$

wherein

A is an alkali metal or an alkaline earth metal or mixture thereof,

M is Mo, W or mixtures thereof, a is about 0.3 to about 10, b is 0.03 to about 5, c is about 0.3 to about 15, z is 0 to about 1 weight percent, and x is the number of oxygen atoms needed to fulfill the valence requirements of the other elements.

15 Claims, No Drawings

MANUFACTURE OF ALCOHOLS FROM SYNTHESIS GAS

BACKGROUND OF THE INVENTION

The present invention is directed to the upgrading of synthesis gas to alcohols. In particular, the present invention is directed to a novel catalyst having a high selectivity to the manufacture of alcohols from synthesis gas.

Since the oil crises of 1973 and 1978, the general price of oil has increased at a rapid rate. As a result of this price increase, chemicals derived from petroleum have become increasingly expensive. Accordingly, alternative sources for use as raw materials in the production of these chemicals have been sought. Synthesis gas is one of the sources being actively pursued as an alternative to petroleum in the production of many chemicals.

Two main types of processes have been proposed for the preparation of alcohols from synthesis gas. First, the modified Fischer and Tropsch synthesis with catalyst and second, the modified methanol synthesis. The present invention is directed to the improvement in the Fischer-Tropsch process.

As a rule, processes of the Fischer and Tropsch type have poor selectivity and productivity. Catalysts which possess acceptable activity in this process generally tend to give a wide spectrum of products, for example, hydrocarbons and oxygenated hydrocarbons having a broad distribution of carbon atom contents. This not only complicates the recovery of desired products, but results in the waste of reactants to commercially uninteresting by-products. Present research has been directed at alleviating these problems.

Recently, in an article by Inoue entitled "Alcohol Synthesis from Syngas on Ruthenium-based Composite Catalysts", *Applied Catalysis*, 11 (1984), pp. 103–116, a ruthenium-molybdenum-sodium supported catalyst is disclosed as useful in the synthesis of alcohols from syngas. In addition, U.S. Pat. Nos. 4,478,955; 4,377,643 and 4,476,247 to Pesa et al disclose ruthenium-copper based catalysts useful in upgrading of synthesis gas. The alkali promoted ruthenium-copper catalyst of the Pesa et al patents produce very little methanol. The higher oxygenates produced are primarily carboxylic acids or aldehydes and an additional hydrogenation step is necessary to arrive at a mixed higher alcohol product. Accordingly, a disadvantage of this patent is the requirement for a second step to produce the higher alcohols. Promotion of the ruthenium-copper system with some Group VIII metals, notably rhodium and iridium, caused the selectivity to shift toward the higher alcohols and away from the acids, but the activity was severely reduced and almost entirely directed to the production of methanol. In addition, the use of rhodium and iridium dramatically increases the costs associated with the process. Accordingly, improvements in the catalyst system disclosed in the Pesa et al patents are desired. Applicants' process and catalyst are directed to an improvement in this system.

SUMMARY OF THE INVENTION

It is an object of the present invention to provide a catalyst for the direct production of alcohols from an economical starting material.

It is another object of the present invention to provide a catalyst for the direct production of alcohols from a mixture of carbon monoxide and hydrogen.

It is a further object of the present invention to provide a process for the direct production of alcohols from a mixture of carbon monoxide and hydrogen.

The term "direct" as used by applicants is intended to mean a single-step process. That is, the production of alcohols from the carbon monoxide and hydrogen source takes place without any additional hydrogenation step as is disclosed in the Pesa et al patent.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects in accordance with the purpose of the present invention as embodied and broadly described herein, the catalyst of the present invention comprises:

$$RuCu_aM_bA_cN_zO_x$$

wherein
A is an alkali metal or an alkaline earth metal or mixture thereof,
M is Mo, W or mixtures thereof,
a is about 0.3 to about 10,
b is 0.03 to about 5,
c is about 0.3 to about 15,
z is 0 to about 1 weight percent, and
x is the number of oxygen atoms needed to fulfill the valence requirements of the other elements.

In a preferred embodiment of the present invention, a is between about 0.3 to 5, b is between about 0.1 to 3 and c is 3 to 10.

In a further aspect of the present invention, a method is provided for the production of alcohols from carbon monoxide and hydrogen comprising contacting carbon monoxide and hydrogen in the vapor phase at an elevated temperature and pressure for a time sufficient to produce the alcohols with a catalyst of the formula:

$$RuCu_aM_bA_cN_zO_x$$

wherein
A is an alkali metal or an alkaline earth metal or mixture thereof,
M is Mo, W or mixtures thereof,
a is about 0.3 to about 10,
b is 0.03 to about 5,
c is about 0.3 to about 15,
z is 0 to about 1 weight percent, and
x is the number of oxygen atoms needed to fulfill the valence requirements of the other elements.

In a preferred embodiment of the present invention, a is between about 0.3 to 5; b is between about 0.1 to 3; and c is about 3 to 10.

In still another aspect of the present invention, a method is provided for the production of alcohols from carbon monoxide and hydrogen comprising contacting carbon monoxide and hydrogen in the vapor phase at an elevated temperature and pressure for a time sufficient to produce the alcohol with a catalyst of the formula $$RuCu_aM_bA_cN_zO_x$$

where
- A is an alkali metal or alkaline earth metal or mixture thereof,
- M is Mo, W or mixtures thereof,
- a is about 0.3 to 10,
- b is about 0.03 to 5,
- c is about 0.3 to 15,
- x is the number of oxygen atoms needed to fulfill the valence requirements of the other elements, wherein the catalyst is prepared by impregnating a porous support with a solution comprising the metal salts of the catalyst components drying the impregnated support and calcining the dried support.

The process of the present invention is directed to the discovery that synthesis gas can be reacted in the presence of the novel catalyst of the present invention in a single step to obtain oxygenate products which comprise a substantial amount of alcohols. In addition, the present invention is directed to the discovery that preparation of the catalyst by impregnation produces extremely high selectivity to alcohols. For example, synthesis gas upgrading by the process of the present invention using a catalyst produced by impregnation results in products where alcohols comprise 97% of the oxygenated products.

DETAILED DESCRIPTION OF THE INVENTION

In the process of the present invention, synthesis gas, or a mixture of carbon monoxide and hydrogen, is reacted in the presence of a carbon monoxide hydrogenation catalyst in the vapor phase to form alcohols. In particular, the process is directed to the upgrading of synthesis gas wherein the procedure has an extremely high selectivity to the production of alcohols.

Synthesis gas may be produced by means known in the art and practiced commercially, including providing synthesis gas as a product of the partial combustion of coal, natural gas, petroleum bottoms or other carbonaceous materials. One method of derivation is the heating of coke in the presence of the air and then steam. The ratio of carbon monoxide to hydrogen in the synthesis gas mixture to be reacted to form the alcohols may vary from 1:10 to 10:1, and is preferably in the range of 1:3 to about 3:1. The synthesis gas may contain a very low amount of sulfur compounds and may also contain small amounts of carbon dioxide, nitrogen and other inerts.

Although synthesis gas is a preferred reactant, any other gas composed primarily of hydrogen and carbon monoxide and having carbon monoxide:hydrogen ratio of 1:10 to 10:1 may be employed. Preferably, the gaseous reactant is essentially sulfur free.

Process Conditions

The process of the present invention is carried out by contacting the gaseous reactants with the novel catalyst described below in a suitable fluid or fixed bed reactor. The reaction can be conducted continuously or in a batch-type operation. The reactor temperature should be maintained from about 220° C. to 400° C., preferably between 250° C. to 350° C.

The reaction pressure should normally be maintained between about 500 to about 10,000 psi, preferably from 500 to 5,000 psi. The reactant gases may be fed to the reactor at a space velocity (defined as liters of gas per liter of catalyst per hour) of about 100 to 10,000 per hour, preferably from about 400 to 6,000.

The contact time of the reactants with the catalyst is generally between about 10 seconds to about 200 seconds, and is preferably about 15 seconds to 140 seconds.

Although the preferred mode of carrying out the process of the present invention is in the vapor phase, the reaction may also be carried out in a slurry operation. Generally, this procedure involves bubbling gaseous C and $H_2$ through a high boiling hydrocarbon slurry containing the catalyst. The reaction temperature, pressure and contact time are substantially the same as set forth above.

Catalyst

The novel catalyst provided by the present invention is believed to be an oxide complex and comprises the composition described by the empirical formula:

$$RuCu_aM_bA_cN_zO_x$$

wherein
- A is an alkali metal or an alkaline earth metal or mixture thereof,
- M is Mo, W or mixtures thereof,
- a is about 0.3 to about 10, preferably about 0.3 to about 5;
- b is 0.03 to about 5, preferably about 0.03 to 3;
- c is about 0.3 to about 15, preferably about 3 to about 10;
- z is 0 to about 1 weight percent, and
- x is the number of oxygen atoms needed to fulfill the valence requirements of the other elements.
- A may be selected from Na, Li, K, Rb, Cs, Be, Mg, Ca, Sr and Ba although Na, K, Li, Rb, Cs and Mg are preferred.

The ratio of Ru to Cu is preferably about 0.1:1 to about 2:1. An oxide of alkali metal or an alkaline earth metal (preferably an alkali metal) is required in the present catalyst. Mixed oxide catalysts of Ru and Cu which are alkali metal and alkaline earth metal free produce essentially all methane. The alkali metal or alkaline earth metal may be present in the catalyst at a level of between 1 to about 15 moles per mole of ruthenium oxide, preferably from about 3 to about 10. Most preferred is a level of about 3 to about 5 mole alkali metal per mole of ruthenium oxide. The level of alkaline earth metal, if present, to ruthenium oxide is preferably 1 to about 5 moles per mole of ruthenium oxide. Preferably the M promoter is present in a level of 0.01 to 3 moles per mole of ruthenium oxide.

The catalyst of the present invention are mixed metal oxides. In the process of the present invention, the catalysts are preferably utilized in a partially reduced state. However, the catalysts may not be totally reduced to the metallic state and thus retains its oxide character.

Catalyst Preparation

The catalyst of the present invention should be formed by impregnation on a carrier. The carrier may possess a high (e.g., 300 m²/g) or low surface area (e.g., 4 m²/g). However, it is preferable that the catalyst of the present invention be formed by impregnation on a carrier having a relatively low surface area (e.g., 1–40 m²/g, most preferably, 1–10 m²/g). Preferably, the carrier is inert and porous and may include a silica, alumina, clay, alumina-silica and the like. The impregnation of the catalyst components on the carrier may be performed by applying a solution of the catalyst component containing compounds onto a carrier, drying and calcining. Usually, the solution of catalyst components is applied through multiply impregnation steps with drying of the support taking place between each step. Alternately, the catalyst components may be added to the carrier separately if desired. That is, a plurality of solutions may be applied each solution comprising at least one different catalyst component in salt form.

The preferred impregnation technique for preparing the catalyst of the present invention is referred to as "Incipient Wetness." In this technique, a nonreducible support is impregnated with an organic or aqueous solution (or several solutions) of metal salts such as chlorides or nitrates. Typically, the salts used are nitrates. In general, the procedure requires dropwise addition of the metal salt solution(s) to 25 cc of support with thorough mixing. When the support is not quite wetted, the catalyst is dried at about 100° to 150° C. for several hours. This procedure is repeated until the desired amount of metal salt solution has been deposited on the support. The impregnated support is then dried overnight and, finally, calcined at about 300° to 400° C. for about 2-5 hours prior to use. Preferably, the calcining is between 325° to 375° C. for about 3 hours.

The catalysts were partially reduced in the following manner. A 20 cc stainless steel tube reactor was packed with catalyst, and hydrogen gas was introduced into the reactor at 150-200 cc/min. at atmospheric pressure. The electric block furnace placed around the reactor was increased in 50° increments stepwise until 500° C. was reached. The final temperature was maintained for two hours, at which time the reactor was allowed to cool with hydrogen flow being continued.

The reduction step can be eliminated with the dried catalyst being placed directly in the reactor for partial reduction.

EXAMPLE 1

Catalyst Preparation

A $Ru_{0.3}CuMo_{0.3}NaO_x$ catalyst was impregnated on a low surface area alumina (4 m²/g). The weight loading of the Ru was approximately 1% by weight. The catalyst was prepared by first impregnating the low surface area alumina with an aqueous solution of the nitrates of Ru, Cu and Na. Typically, the solution comprised 2.84 g of an 8% aqueous solution of $Ru(NO_3)_3$, 1.81 g $Cu(NO_3)_2$ and about 0.63 g $NaNO_3$ and about 4.66 g $H_2O$. The catalyst impregnated with this solution was dried and calcined at 350° C. for 3 hours. A second solution comprising 8 g $H_2O$ and 0.4 g Ammonium Heptamolybdate was added dropwise to the calcined support. The resulting catalyst was dried overnight at 125° C. and calcined for 3 hours at 350° C. The catalysts were partially reduced in the following manner. A 20 cc stainless steel tube reactor was packed with catalyst, and hydrogen gas was introduced into the reactor at 150-200 cc/min. at atmospheric pressure. The electric block furnace placed around the reactor was increased in 50° increments stepwise until 500° C. was reached. The final temperature was maintained for two hours, at which time the reactor was allowed to cool with hydrogen flow being continued. The catalyst was now ready for use.

Reaction Procedure

Following catalyst preparation and subsequent cooling to room temperature, the reactor was charged to the desired pressure with hydrogen (1300 psi). The temperature was raised to about 325° C. and a gaseous mixture of carbon monoxide and hydrogen was passed over the catalyst at a space velocity of 2,000 liters/liters/hour. The ratio of the carbon monoxide to hydrogen in the reactor was about 1:1.

Gas chromatograph analysis of the resulting products indicated that the carbon monoxide conversion was about 35%. The weight selectivity to alcohols was 61%. Of the alcohols, 77% are higher alcohols ($C_2$ or greater) and the alcohols comprise 97% of the oxygenated products.

EXAMPLE 2

For comparison purposes, the following example was run using a catalyst which did not contain Mo or W. The procedures set forth in Example 1 were followed (except that a reaction temperature of 300° C. was used) using a catalyst having the following composition:

$$Ru_{0.3}CuNaO_x$$

The resulting produce gave a 59% selectivity to oxygenates. Of these oxygenates, specific selectivity was 37% acid, 7% alcohol and 16% aldehydes. A comparison of Examples 1 and 2 clearly demonstrates the superior selectivity to alcohols attributed to the catalyst of the present invention.

Example 3 set forth below provides a direct comparison of a catalyst prepared by impregnation versus a coated version of the Mo promoted catalyst.

EXAMPLE 3

Two catalysts with 3% ruthenium loading were prepared and tested under identical conditions. Catalyst A was prepared by coating the catalyst of composition $RuCuMo_{0.1}Na_{0.2-0.3}O_x$ on a low surface area support comprising Norton SA 5223 Alundum ® (e.g., 0.1 m²/g). The coating procedure is described in U.S. Pat. No. 4,077,912 herein incorporated by reference. Catalyst B was prepared by impregnating a solution of composition $RuCuMo_{0.1}NaO_x$ by the impregnation technique described in Example 4. Both catalysts were tested under identical conditions of 320° C., 1000 psi, 3:7 $CO:H_2$ ratio and 5500 1/1/hr. The results are set forth below in Table I.

TABLE I

| | CO Conv. | Paraffins | Olefins | Acids | Alcohols | Aldehydes |
|---|---|---|---|---|---|---|
| A Coated | 15.1 | 61.4 | 23.2 | 9.0 | 8.3 | 0.0 |
| B Impregnated | 19.1 | 30.6 | 24.6 | 6.2 | 31.6 | 7.0 |

As can be readily seen from Table I, the alcohol selectivity is significantly improved with the catalyst prepared via impregnation.

EXAMPLE 4

(Single Step Impregnation)

A $RuCuMo_{0.1}NaO_x$ catalyst was impregnated on low surface area alumina (4 m²/g). The weight loading of the Ru was approximately 3% by weight. The catalyst was prepared by impregnating 10/30 mesh particles which had been previously dried for 3 hours at 125° C. Typically, a solution of 7.54 g of aqueous ruthenium nitrate (8% by weight ruthenium), 1.81 g copper nitrate, 0.63 g sodium nitrate, and 0.11 g $MoO_3$ was used. The catalyst was dried and calcined at 350° C. for 3 hours. The reduction procedure was identical to that described for Example 1. The results are set forth below in Table II.

In addition, Table II contains the results of examples with various identified catalyst of the present invention. The catalyst identified in the Table were all prepared by substantially the same impregnation technique described in Example 4. The examples were performed under various conditions to provide a true representation of the improved selectivity of the catalyst of the present invention to the production of alcohols.

TABLE II

| Example No. | Catalyst Composition | Temp | Press | CO:$H_2$ | GHSV | Conv | Alcohol | Total Oxygenates |
|---|---|---|---|---|---|---|---|---|
| 4 | $RuCuMo_{.1}Na/LSAA$ | 300 | 1300 | 3:7 | 3300 | 59.8 | 28.4 | 42.6 |
| 5 | $RuCuMo_{.1}Na/LSAA$ | 270 | 1300 | 3:7 | 2000 | 15.4 | 12.3 | 33.1 |
| 6 | $RuCuMo_{.1}Na/LSAA$ | 280 | 1300 | 3:7 | 3300 | 16.0 | 27.8 | 41.9 |
| 7 | $RuCuMo_{.1}Na/LSAA$ | 280 | 1300 | 3:7 | 2000 | 26.4 | 35.3 | 47.7 |
| 8 | $RuCuMo_{.1}Na/LSAA$ | 290 | 1300 | 3:7 | 2000 | 38.3 | 31.4 | 44.5 |
| 9 | $RuCuMo_{.03}Na/LSAA$ | 300 | 1300 | 3:7 | 3300 | 56.7 | 24.9 | 45.1 |
| 10 | $RuCuMo_{.03}Na/LSAA$ | 300 | 1300 | 3:7 | 5000 | 17.5 | 22.3 | 49.3 |
| 11 | $RuCuMo_{.03}Na/LSAA$ | 280 | 1300 | 3:7 | 5000 | 9.0 | 16.6 | 51.0 |
| 12 | $RuCuMo_{.03}Na/LSAA$ | 280 | 1300 | 3:7 | 2000 | 19.7 | 24.9 | 52.6 |
| 13 | $RuCuMo_{.03}Na/LSAA$ | 300 | 1300 | 3:7 | 2000 | 34.2 | 33.1 | 60.6 |
| 14 | $RuCuMo_{.03}Na/LSAA$ | 270 | 1300 | 3:7 | 2000 | 9.4 | 25.2 | 54.4 |
| 15 | $RuCuMoNa/LSAA$ | 305 | 1300 | 3:7 | 3300 | 60.6 | 32.0 | 39.8 |
| 16 | $RuCuMoNa/LSAA$ | 280 | 1300 | 3:7 | 2000 | 25.5 | 19.2 | 35.4 |
| 17 | $RuCuMoNa/LSAA$ | 280 | 1300 | 3:7 | 5000 | 12.0 | 18.3 | 36.4 |
| 18 | $RuCuMoNa/LSAA$ | 260 | 1300 | 3:7 | 2000 | 4.6 | 18.3 | 30.0 |
| 19 | $RuCuMo_{0.3}Na/LSAA$ | 300 | 1300 | 3:7 | 3300 | 66.7 | 32.0 | 45.1 |
| 20 | $RuCuMo_{0.3}Na/LSAA$ | 300 | 1300 | 3:7 | 3300 | 48.5 | 37.9 | 49.2 |
| 21 | $RuCuMo_{0.3}Na/LSAA$ | 300 | 1300 | 3:7 | 3300 | 44.5 | 33.4 | 45.9 |
| 22 | $RuCuMo_{0.3}Na/LSAA$ | 300 | 1300 | 3:7 | 3300 | 42.3 | 31.0 | 44.8 |
| 23 | $RuCuMo_{0.3}Na/LSAA$ | 300 | 1300 | 3:7 | 3300 | 46.5 | 36.4 | 47.6 |
| 24 | $RuCuMo_{0.3}Na/LSAA$ | 300 | 1300 | 1:1 | 3300 | 19.5 | 38.0 | 55.4 |
| 25 | $RuCuMo_{0.3}Na/LSAA$ | 310 | 1300 | 3:7 | 2000 | 85.3 | 34.6 | 41.4 |
| 26 | $RuCuMo_{0.3}Na/LSAA$ | 310 | 1300 | 1:1 | 2000 | 42.9 | 34.0 | 48.0 |
| 27 | $RuCuMo_{0.3}Na/LSAA$ | 290 | 1300 | 1:1 | 2000 | 25.1 | 38.3 | 48.9 |
| 28 | $Ru_{0.3}CuMo_{0.3}Na/LSAA$ | 325 | 1300 | 3:7 | 3300 | 47.1 | 35.8 | 42.6 |
| 29 | $Ru_{0.3}CuMo_{0.3}Na/LSAA$ | 325 | 1300 | 3:7 | 3300 | 41.8 | 50.4 | 57.1 |
| 30 | $Ru_{0.3}CuMo_{0.3}Na/LSAA$ | 325 | 1300 | 3:7 | 3300 | 41.5 | 45.4 | 56.4 |
| 31 | $Ru_{0.3}CuMo_{0.3}Na/LSAA$ | 325 | 1300 | 1:1 | 3300 | 23.9 | 57.2 | 61.2 |
| 32 | $Ru_{0.3}CuMo_{0.3}Na/LSAA$ | 325 | 1300 | 7:3 | 3300 | 18.3 | 62.8 | 66.7 |
| 33 | $Ru_{0.3}CuMo_{0.3}Na/LSAA$ | 325 | 1300 | 1:1 | 2000 | 35.3 | 60.7 | 62.8 |
| 34 | $Ru_{0.3}CuMo_{0.3}Na/LSAA$ | 325 | 1300 | 7:3 | 2000 | 14.8 | 51.9 | 55.5 |
| 35 | $Ru_{0.3}CuMo_{0.3}Na/LSAA$ | 310 | 1300 | 1:1 | 2000 | 18.5 | 61.7 | 63.8 |
| 36 | $Ru_{0.3}CuMo_{0.3}Na/LSAA$ | 310 | 1300 | 7:3 | 2000 | 13.2 | 49.1 | 51.9 |
| 37 | $Ru_{0.3}CuMo_{0.3}Na/LSAA$ | 325 | 1300 | 3:7 | 5000 | 37.8 | 50.5 | 51.9 |
| 38 | $Ru_{0.3}Cu_2Mo_{0.3}Na/LSAA$ | 325 | 1300 | 3:7 | 3300 | 39.9 | 57.8 | 65.6 |
| 39 | $Ru_{0.3}Cu_2Mo_{0.3}Na/LSAA$ | 325 | 1300 | 3:7 | 3300 | 37.1 | 41.1 | 47.7 |
| 40 | $Ru_{0.3}Cu_2Mo_{0.3}Na/LSAA$ | 325 | 1300 | 1:1 | 3300 | 15.9 | 58.7 | 64.2 |
| 41 | $Ru_{0.3}Cu_2Mo_{0.3}Na/LSAA$ | 325 | 1300 | 1:1 | 3300 | 19.3 | 65.4 | 70.1 |
| 42 | $Ru_{0.3}Cu_2Mo_{0.3}Na/LSAA$ | 325 | 1300 | 7:3 | 3300 | 10.2 | 47.8 | 52.2 |
| 43 | $Ru_{0.3}Cu_2Mo_{0.3}Na/LSAA$ | 325 | 1300 | 3:7 | 2000 | 49.8 | 43.6 | 44.6 |
| 44 | $Ru_{0.3}Cu_2Mo_{0.3}Na/LSAA$ | 325 | 1300 | 1:1 | 2000 | 33.1 | 47.1 | 51.8 |
| 45 | $Ru_{0.3}CuMo_{0.3}Na/LSAA$ | 330 | 1300 | 3:7 | 3300 | 64.1 | 39.0 | 46.2 |
| 46 | $Ru_{0.3}CuMo_{0.3}Na/LSAA$ | 310 | 1300 | 1:1 | 2000 | 21.2 | 33.2 | 54.8 |
| 47 | $Ru_{0.3}CuMo_{0.3}Na/LSAA$ | 310 | 1300 | 1:1 | 2000 | 19.4 | 40.0 | 52.5 |
| 48 | $Ru_{0.3}CuMo_{0.3}Na/LSAA$ | 330 | 1300 | 1:1 | 2000 | 38.3 | 56.4 | 60.1 |
| 49 | $Ru_{0.3}CuMo_{0.3}Na/LSAA$ | 330 | 1300 | 1:1 | 2000 | 37.6 | 45.0 | 53.4 |
| 50 | $Ru_{0.3}CuMo_{0.3}Na/LSAA$ | 330 | 1300 | 1:1 | 2000 | 31.1 | 49.2 | 52.6 |
| 51 | $Ru_{0.3}CuMo_{0.3}Na/LSAA$ | 330 | 1000 | 1:1 | 2000 | 28.4 | 51.4 | 57.3 |
| 52 | $Ru_{0.3}CuMo_{0.3}Na/LSAA$ | 330 | 700 | 1:1 | 2000 | 22.4 | 43.0 | 46.8 |
| 53 | $Ru_{0.3}CuMo_{0.3}Na/LSAA$ | 330 | 400 | 1:1 | 2000 | 12.7 | 38.6 | 40.5 |
| 54 | $Ru_{0.3}CuMo_{0.3}Na/LSAA$ | 330 | 1300 | 3:7 | 3300 | 66.1 | 46.4 | 48.7 |
| 55 | $Ru_{0.3}CuMo_{0.3}Na/LSAA$ | 330 | 1300 | 1:1 | 2000 | 44.5 | 54.1 | 57.5 |
| 56 | $Ru_{0.3}CuMo_{0.3}Na/LSAA$ | 330 | 1300 | 1:1 | 2000 | 40.1 | 50.0 | 52.8 |
| 57 | $Ru_{0.3}CuMo_{0.3}Na/LSAA$ | 320 | 1300 | 1:1 | 2000 | 29.1 | 54.2 | 56.3 |
| 58 | $Ru_{0.3}CuMo_{0.3}Na/LSAA$ | 310 | 1300 | 1:1 | 2000 | 20.8 | 58.2 | 60.3 |
| 59 | $Ru_{0.3}CuMo_{0.3}Na/LSAA$ | 300 | 1300 | 1:1 | 2000 | 17.2 | 57.2 | 59.6 |
| 60 | $Ru_{0.3}CuMo_{0.3}Na/LSAA$ | 310 | 1300 | 1:1 | 3500 | 10.7 | 52.6 | 54.8 |
| 61 | $Ru_{0.3}CuMo_{0.3}Na/LSAA$ | 310 | 1300 | 1:1 | 5000 | 12.5 | 59.5 | 61.7 |
| 62 | $Ru_{0.3}CuMo_{0.3}Na/LSAA$ | 310 | 1300 | 1:1 | 5000 | 12.4 | 56.8 | 59.1 |
| 63 | $Ru_{0.3}CuMo_{0.3}Na/LSAA$ | 310 | 1300 | 1:1 | 6500 | 9.5 | 58.1 | 60.0 |
| 64 | $Ru_{0.3}CuMo_{0.3}Na/LSAA$ | 310 | 1300 | 3:7 | 2000 | 34.5 | 51.2 | 52.5 |
| 65 | $Ru_{0.3}CuMo_{0.3}Na/LSAA$ | 310 | 1300 | 3:7 | 2000 | 46.0 | 50.2 | 51.9 |
| 66 | $Ru_{0.3}CuMo_{0.3}Na/LSAA$ | 310 | 1300 | 5:7 | 2000 | 25.9 | 56.1 | 58.0 |
| 67 | $Ru_{0.3}CuMo_{0.3}Na/LSAA$ | 310 | 1300 | 6:7 | 2000 | 23.5 | 52.1 | 53.8 |
| 68 | $Ru_{0.3}CuMo_{0.3}Na/LSAA$ | 310 | 1300 | 7:7 | 2000 | 25.3 | 55.9 | 57.1 |
| 69 | $Ru_{0.3}CuMo_{0.3}Na/LSAA$ | 310 | 1300 | 7:6 | 2000 | 22.3 | 55.9 | 57.6 |
| 70 | $Ru_{0.3}CuMo_{0.3}Na/LSAA$ | 310 | 1300 | 7:5 | 2000 | 8.6 | 54.3 | 55.9 |
| 71 | $Ru_{0.3}CuMo_{0.3}Na/LSAA$ | 310 | 1300 | 7:3 | 2000 | 13.8 | 55.1 | 57.0 |
| 72 | $Ru_{0.3}CuMo_{0.3}Na/LSAA$ | 330 | 1300 | 1:1 | 2000 | 43.5 | 44.4 | 46.4 |
| 73 | $Ru_{0.3}CuMo_{0.3}Na/LSAA$ | 310 | 1600 | 1:1 | 2000 | 27.0 | 56.8 | 57.9 |
| 74 | $Ru_{0.3}CuMo_{0.3}Na/LSAA$ | 310 | 1300 | 1:1 | 2000 | 18.0 | 46.3 | 47.2 |

TABLE II-continued

| Example No. | Catalyst Composition | Temp | Press | CO:H$_2$ | GHSV | Conv | Alcohol | Total Oxygenates |
|---|---|---|---|---|---|---|---|---|
| 75 | Ru$_{0.3}$CuMo$_{0.2}$Na/LSAA | 320 | 1300 | 1:1 | 2000 | 38.7 | 48.5 | 55.4 |
| 76 | Ru$_{0.3}$CuMo$_{0.2}$Na/LSAA | 300 | 1300 | 1:1 | 2000 | 14.4 | 49.1 | 51.8 |
| 77 | Ru$_{0.3}$CuMo$_{0.2}$Na/LSAA | 310 | 1300 | 1:1 | 2000 | 19.6 | 50.6 | 52.8 |
| 78 | Ru$_{0.3}$CuMo$_{0.3}$Na/LSAA | 330 | 1300 | 1:1 | 2000 | 42.9 | 52.8 | 58.3 |
| 79 | Ru$_{0.3}$CuMo$_{0.3}$Na/LSAA | 310 | 1300 | 1:1 | 2000 | 22.5 | 49.7 | 52.3 |
| 80 | Ru$_{0.3}$CuMo$_{0.3}$Na/LSAA | 310 | 1300 | 7:3 | 2000 | 9.3 | 38.2 | 41.5 |
| 81 | Ru$_{0.3}$CuMo$_{0.3}$K/LSAA | 330 | 1300 | 1:1 | 2000 | 25.9 | 40.8 | 48.4 |
| 82 | Ru$_{0.3}$CuMo$_{0.3}$K/LSAA | 340 | 1300 | 1:1 | 2000 | 29.8 | 46.4 | 51.3 |
| 83 | Ru$_{0.3}$CuMo$_{0.3}$K/LSAA | 320 | 1300 | 1:1 | 2000 | 18.3 | 44.3 | 48.4 |
| 84 | Ru$_{0.3}$CuMo$_{0.3}$Na$_{0.75}$/LSAA | 330 | 1300 | 1:1 | 2000 | 50.0 | 41.8 | 52.1 |
| 85 | Ru$_{0.3}$CuMo$_{0.3}$Na$_{0.75}$/LSAA | 310 | 1300 | 1:1 | 2000 | 22.3 | 44.0 | 50.3 |
| 86 | Ru$_{0.3}$CuMo$_{0.3}$Na$_{0.75}$/LSAA | 310 | 1300 | 7:3 | 2000 | 10.2 | 35.6 | 44.1 |

Table III set forth below contains the results of the following examples prepared by the impregnation techniques described below.

EXAMPLE 87

A Ru$_{0.3}$CuNa$_{1.6}$O$_x$ catalyst was prepared by impregnation of an aqueous solution of the nitrates of Ru, Cu and Na. The catalyst was dried and calcined at 350° C. for 3 hours. A second solution comprising 7 g of water and 0.54 g of Na$_2$MoO$_4$ was added dropwise to the calcined support. The resulting catalyst was dried overnight at 125° C. and calcined at 350° C. for 3 hours. The reduction procedure was identical to that described in Example 1.

EXAMPLES 88-91

A Ru$_{0.3}$CuNa$_{1.6}$O$_x$ catalyst was prepared by impregnation of an aqueous solution of the nitrates of Ru, Cu and Na. The catalyst was dried and calcined at 350° C. for 3 hours. The catalyst was then reduced according to the procedure described in Example 1. A second solution comprising 7 g of water and 0.54 g of Na$_2$MoO$_4$ was added dropwise to the reduced catalyst. The resulting catalyst was dried overnight at 125° C. and calcined at 350° C. for 3 hours. The catalyst was then reduced again according to the procedure in Example 1.

EXAMPLES 92-94

The Ru$_{0.3}$CuMo$_{0.3}$Na$_{1.6}$ catalyst of these examples were prepared by first impregnating a low surface alumina support with an aqueous solution of Na$_2$MoO$_4$, drying and calcining. Then a second impregnating solution of the nitrates of Ru, Cu and Na was introduced. The catalyst was then dried, calcined and reduced according to Example 1. Typically, an aqueous solution of 0.65 g of Na$_2$MoO$_4$ in 8 g of water was used for the first impregnating, and a solution of 2.84 g of aqueous ruthenium nitrate (8% Ru), 1.81 g copper nitrate, 0.63 g of sodium nitrate, and approximately 4.66 g water was used for the second impregnating solution.

EXAMPLES 95-97

A Ru$_{0.3}$CuMo$_{0.3}$Na catalyst was prepared according to the procedure described in Examples 88-91.

TABLE III

| Example No. | Catalyst Composition | Temp | Press | CO:H$_2$ | GHSV | Conv | Alcohol | Total Oxygenates |
|---|---|---|---|---|---|---|---|---|
| 87 | Ru$_{0.3}$CuMo$_{0.3}$Na$_{1.6}$/LSAA | 310 | 1300 | 1:1 | 2000 | 15.6 | 51.5 | 52.5 |
| 88 | Ru$_{0.3}$CuMo$_{0.3}$Na$_{1.6}$/LSAA | 350 | 1300 | 1:1 | 2000 | 28.1 | 32.4 | 33.1 |
| 89 | Ru$_{0.3}$CuMo$_{0.3}$Na$_{1.6}$/LSAA | 310 | 1600 | 1:1 | 2000 | 8.0 | 56.1 | 57.1 |
| 90 | Ru$_{0.3}$CuMo$_{0.3}$Na$_{1.6}$/LSAA | 310 | 1300 | 1:1 | 2000 | 8.6 | 60.2 | 61.6 |
| 91 | Ru$_{0.3}$CuMo$_{0.3}$Na$_{1.6}$/LSAA | 310 | 1300 | 7:5 | 2000 | 5.5 | 48.5 | 49.7 |
| 92 | Ru$_{0.3}$CuMo$_{0.3}$Na$_{1.6}$/LSAA | 350 | 1300 | 1:1 | 2000 | 37.1 | 28.5 | 29.2 |
| 93 | Ru$_{0.3}$CuMo$_{0.3}$Na$_{1.6}$/LSAA | 310 | 1300 | 1:1 | 2000 | 12.7 | 54.3 | 56.0 |
| 94 | Ru$_{0.3}$CuMo$_{0.3}$Na$_{1.6}$/LSAA | 330 | 1300 | 1:1 | 2000 | 19.8 | 39.7 | 40.6 |
| 95 | Ru$_{0.3}$CuMo$_{0.3}$Na/LSAA | 330 | 1300 | 1:1 | 2000 | 30.8 | 49.2 | 51.2 |
| 96 | Ru$_{0.3}$CuMo$_{0.3}$Na/LSAA | 310 | 1300 | 1:1 | 2000 | 17.4 | 51.3 | 53.1 |
| 97 | Ru$_{0.3}$CuMo$_{0.3}$Na/LSAA | 320 | 1300 | 1:1 | 2000 | 21.4 | 52.1 | 54.2 |

Table IV set forth below contains the results of the following examples prepared by the impregnation techniques described below.

EXAMPLES 98-103

Ru$_{0.3}$CuMo$_{0.3}$Na catalyst were prepared similarly to Example 4, except that the supports were varied. These included an activated alumina (HSAA), a medium surface area alumina (MSAA), and a silica gel (SiO$_x$). The catalysts were reduced as in Example 1.

TABLE IV

| Example No. | Catalyst Composition | Temp | Press | CO:H$_2$ | GHSV | Conv | Alcohol | Total Oxygenates |
|---|---|---|---|---|---|---|---|---|
| 98 | Ru$_{0.3}$CuMo$_{0.3}$Na/HSAA | 280 | 1300 | 3:7 | 3300 | 22.7 | 28.3 | 31.4 |
| 99 | Ru$_{0.3}$CuMo$_{0.3}$Na/HSAA | 305 | 1300 | 3:7 | 3300 | 28.0 | 24.3 | 25.1 |
| 100 | Ru$_{0.3}$CuMo$_{0.3}$Na/MSAA | 320 | 1300 | 1:1 | 3300 | 20.0 | 47.0 | 48.1 |
| 101 | Ru$_{0.3}$CuMo$_{0.3}$Na/MSAA | 305 | 1300 | 1:1 | 2000 | 15.9 | 57.3 | 58.3 |
| 102 | Ru$_{0.3}$CuMo$_{0.3}$Na/SiOx | 315 | 1300 | 1:1 | 2000 | 29.3 | 37.4 | 41.7 |
| 103 | Ru$_{0.3}$CuMo$_{0.3}$Na/SiOx | 305 | 1300 | 1:1 | 2000 | 16.1 | 49.4 | 56.8 |

Table V set forth below contains the results of the following examples prepared by the impregnation technique described below.

EXAMPLES 104-106

The Ru$_{0.3}$CuMo$_{0.3}$Na$_{0.75}$ catalyst were prepared according to the procedure set forth in Example 4, except that the reduction was kept at 500° C. for 5 hours instead of 2 hours.

TABLE V

| Example No. | Catalyst Composition | Temp | Press | CO:H$_2$ | GHSV | Conv | Alcohol | Total Oxygenates |
|---|---|---|---|---|---|---|---|---|
| 104 | Ru$_{0.3}$CuMo$_{0.3}$Na$_{0.75}$/LSAA | 340 | 1300 | 1:1 | 2000 | 53.7 | 41.3 | 45.8 |
| 105 | Ru$_{0.3}$CuMo$_{0.3}$Na$_{0.75}$/LSAA | 310 | 1300 | 1:1 | 2000 | 28.5 | 47.7 | 53.3 |
| 106 | Ru$_{0.3}$CuMo$_{0.3}$Na$_{0.75}$/LSAA | 320 | 1300 | 1:1 | 2000 | 27.5 | 41.8 | 45.5 |

Tabe VI set forth below contains the results obtained from the following examples. The impregnation techniques used in preparing each composition are discussed below.

EXAMPLES 107–137

The catalysts prepared in these examples followed substantially the same procedure described in Example 1 above. The only changes are in the molar ratios of the elements.

EXAMPLES 138 AND 139

These catalysts were prepared similarly to Example 1. They were reduced in the stepwise standard method, except it was done in the reactor rather than a separate reducer tube. This was to prevent any exposure to air after reduction.

EXAMPLES 140–142

These catalysts were prepared similarly to Example 1. They were reduced stepwise in 50° C. increments to 250° C. in flowing hydrogen then to 500° C. in CO/H$_2$, and kept at 500° C. for 5 hours.

EXAMPLE 143

These catalysts were prepared similarly to Example 1. They were reduced by the standard method to 500° C. in flowing hydrogen. They were then heated at 500° C. for 2 hours in flowing CO.

EXAMPLES 144–146

These catalysts were prepared similarly to Example 1. They were reduced by the standard method to 500° C. in flowing hydrogen. They were then heated at 500° C. in flowing nitrogen for 5 hours.

EXAMPLES 147–149

These catalysts were prepared similarly to Example 1 with the following differences. After impregnation of the Ru, Cu and Na, the sample was dried and reduced by the standard method to 500° C., as described in Example 1. (The samples were not calcined before reduction.) The Mo was impregnated as in Example 1 and the catalysts were immediately tested. (They were not calcined or reduced after Mo impregnation, only dried.)

EXAMPLES 150 AND 151

These catalysts were identically prepared to Examples 147–149, except that the catalyst was calcined after the Ru, Cu, Na impregnation. (Examples 147–149 were not.)

EXAMPLES 152 AND 153

These catalysts were prepared similarly to Example 87, except that they were reduced by standard method, as described in Example 1, after the Ru, Cu, Na impregnation and calcination, but before the Mo impregnation. After the Mo impregnation, the catalysts were immediately tested, without reduction.

EXAMPLES 154 AND 155

These catalysts were prepared similarly to Example 152 and 153, except that the samples were not calcined after Ru, Cu, Na impregnation. They were dried and then reduced. Otherwise it is the same as Examples 152 and 153.

EXAMPLES 156–158

To 50 g of −150 mesh activated alumina which had been dried 10 hours at 125° C. was added dropwise a solution of 6.40 g of sodium nitrate in 16 g of water. The sample was dried and calcined. One-half of this support was impregnated with an aqueous solution made of 5.68 g of aqueous ruthenium nitrate solution (8% Ru), 7.24 g copper nitrate, 1.28 g sodium nitrate, and about 15 g water. The other half of the support was impregnated with a solution of 1.08 g sodium molybdate and about 8 g of water. After drying and calcining, this half was combined with the first half, pelleted and reduced stepwise in hydrogen in the standard manner, as described in Example 1.

TABLE VI

| Example No. | Catalyst Composition | Temp | Press | Co:H$_2$ | GHSV | Conv | Alcohol | Total Oxygenates |
|---|---|---|---|---|---|---|---|---|
| 107 | Ru$_{0.3}$CuMo$_{0.3}$Na/LSAA | 330 | 1300 | 1:1 | 2000 | 48.2 | 47.4 | 50.9 |
| 108 | Ru$_{0.3}$CuMo$_{0.3}$Na/LSAA | 310 | 1300 | 1:1 | 2000 | 16.7 | 45.6 | 47.2 |
| 109 | Ru$_{0.3}$CuMo$_{0.3}$Na/LSAA | 310 | 1300 | 7:3 | 2000 | 10.6 | 54.7 | 58.1 |
| 110 | Ru$_{0.3}$CuMo$_{0.7}$Na/LSAA | 330 | 1300 | 1:1 | 2000 | 39.7 | 46.2 | 50.3 |
| 111 | Ru$_{0.3}$CuMo$_{0.7}$Na/LSAA | 330 | 1300 | 7:3 | 2000 | 17.6 | 31.9 | 37.1 |
| 112 | Ru$_{0.3}$CuMo$_{0.7}$Na/LSAA | 340 | 1300 | 7:3 | 2000 | 15.3 | 41.6 | 45.3 |
| 113 | Ru$_{0.3}$CuMo$_{0.1}$Na/LSAA | 330 | 1300 | 1:1 | 2000 | 41.2 | 55.6 | 59.1 |
| 114 | Ru$_{0.3}$CuMo$_{0.1}$Na/LSAA | 310 | 1300 | 1:1 | 2000 | 21.5 | 32.9 | 34.6 |
| 115 | Ru$_{0.3}$CuMo$_{0.1}$Na/LSAA | 320 | 1300 | 7:3 | 2000 | 22.9 | 28.2 | 30.2 |
| 116 | Ru$_{0.3}$CuMo$_{0.1}$Na/LSAA | 320 | 1300 | 1:1 | 2000 | 40.4 | 51.6 | 54.3 |
| 117 | Ru$_{0.3}$CuMo$_{0.3}$Na/LSAA | 330 | 1300 | 1:1 | 2000 | 35.4 | 44.3 | 45.6 |
| 118 | Ru$_{0.3}$CuMo$_{0.3}$Na/LSAA | 310 | 1300 | 1:1 | 2000 | 15.3 | 52.4 | 53.6 |
| 119 | Ru$_{0.3}$CuMo$_{0.3}$Na/LSAA | 320 | 1300 | 1:1 | 2000 | 37.7 | 48.5 | 50.4 |
| 120 | Ru$_{0.3}$CuMo$_{0.3}$Na/LSAA | 310 | 1300 | 1:1 | 2000 | 30.0 | 55.9 | 56.7 |
| 121 | Ru$_{0.3}$CuMo$_{0.01}$Na/LSAA | 330 | 1300 | 1:1 | 2000 | 73.4 | 18.5 | 57.7 |
| 122 | Ru$_{0.3}$CuMo$_{0.01}$Na/LSAA | 320 | 1300 | 7:3 | 2000 | 28.2 | 0.0 | 0.0 |
| 123 | Ru$_{0.3}$CuMo$_{0.01}$Na/LSAA | 320 | 1300 | 1:1 | 2000 | 24.0 | 5.6 | 10.8 |
| 124 | Ru$_{0.3}$CuMo$_{0.01}$Na/LSAA | 340 | 1300 | 1:1 | 2000 | 46.1 | 28.7 | 54.7 |
| 125 | Ru$_{0.3}$CuMo$_{0.3}$Na/LSAA | 330 | 1300 | 1:1 | 2000 | 65.6 | 61.0 | 63.6 |
| 126 | Ru$_{0.3}$CuMo$_{0.3}$Na/LSAA | 320 | 1300 | 3:7 | 2000 | 61.7 | 5.6 | 5.9 |
| 127 | Ru$_{0.3}$CuMo$_{0.3}$Na/LSAA | 320 | 1300 | 3:7 | 2000 | 50.0 | 50.1 | 50.3 |
| 128 | Ru$_{0.3}$CuMo$_{0.3}$Na/LSAA | 310 | 1300 | 5:7 | 2000 | 33.7 | 47.1 | 48.1 |

TABLE VI-continued

| Example No. | Catalyst Composition | Temp | Press | Co:H$_2$ | GHSV | Conv | Alcohol | Total Oxygenates |
|---|---|---|---|---|---|---|---|---|
| 129 | Ru$_{0.3}$CuMo$_{0.3}$Na/LSAA | 330 | 1300 | 3:7 | 2000 | 53.8 | 47.4 | 49.1 |
| 130 | Ru$_{0.3}$CuMo$_{0.3}$Na/LSAA | 330 | 1300 | 5:7 | 2000 | 46.5 | 41.4 | 43.5 |
| 131 | Ru$_{0.3}$CuMo$_{0.3}$Na/LSAA | 310 | 1300 | 3:7 | 2000 | 35.2 | 48.3 | 49.9 |
| 132 | Ru$_{0.3}$CuMo$_{0.03}$Na/LSAA | 330 | 1300 | 1:1 | 2000 | 46.1 | 35.7 | 58.4 |
| 133 | Ru$_{0.3}$CuMo$_{0.03}$Na/LSAA | 320 | 1300 | 1:1 | 2000 | 29.9 | 35.0 | 53.4 |
| 134 | Ru$_{0.3}$CuMo$_{0.03}$Na/LSAA | 320 | 1300 | 3:7 | 2000 | 25.6 | 29.0 | 37.3 |
| 135 | Ru$_{0.3}$CuMo$_{0.05}$Na/LSAA | 330 | 1300 | 1:1 | 2000 | 29.7 | 36.5 | 50.0 |
| 136 | Ru$_{0.3}$CuMo$_{0.05}$Na/LSAA | 320 | 1300 | 1:1 | 2000 | 9.0 | 38.2 | 45.3 |
| 137 | Ru$_{0.3}$CuMo$_{0.05}$Na/LSAA | 330 | 1300 | 3:7 | 2000 | 17.4 | 49.8 | 53.7 |
| 138 | Ru$_{0.3}$CuMo$_{0.3}$Na/LSAA | 330 | 1300 | 1:1 | 2000 | 26.4 | 46.2 | 47.3 |
| 139 | Ru$_{0.3}$CuMo$_{0.3}$Na/LSAA | 310 | 1300 | 1:1 | 2000 | 13.4 | 52.1 | 54.1 |
| 140 | Ru$_{0.3}$CuMo$_{0.3}$Na/LSAA | 330 | 1300 | 3:7 | 2000 | 7.0 | 28.8 | 30.2 |
| 141 | Ru$_{0.3}$CuMo$_{0.3}$Na/LSAA | 340 | 1300 | 3:7 | 2000 | 23.6 | 36.9 | 40.1 |
| 142 | Ru$_{0.3}$CuMo$_{0.3}$Na/LSAA | 340 | 1300 | 1:1 | 2000 | 13.9 | 0.0 | 0.0 |
| 143 | Ru$_{0.3}$CuMo$_{0.3}$Na/LSAA | 360 | 1300 | 1:1 | 2000 | 20.4 | 17.6 | 18.4 |
| 144 | Ru$_{0.3}$CuMo$_{0.3}$Na/LSAA | 340 | 1300 | 1:1 | 2000 | 27.9 | 36.6 | 37.5 |
| 145 | Ru$_{0.3}$CuMo$_{0.3}$Na/LSAA | 330 | 1300 | 1:1 | 2000 | 26.9 | 30.9 | 32.3 |
| 146 | Ru$_{0.3}$CuMo$_{0.3}$Na/LSAA | 340 | 1300 | 1:1 | 2000 | 33.6 | 38.1 | 39.1 |
| 147 | Ru$_{0.3}$CuMo$_{0.3}$Na/LSAA | 330 | 1300 | 1:1 | 2000 | 25.6 | 49.0 | 52.7 |
| 148 | Ru$_{0.3}$CuMo$_{0.3}$Na/LSAA | 340 | 1300 | 1:1 | 2000 | 32.9 | 35.6 | 38.5 |
| 149 | Ru$_{0.3}$CuMo$_{0.3}$Na/LSAA | 340 | 1300 | 3:7 | 2000 | 47.6 | 40.2 | 42.7 |
| 150 | Ru$_{0.3}$CuMo$_{0.3}$Na/LSAA | 330 | 1300 | 1:1 | 2000 | 38.5 | 4.8 | 51.7 |
| 151 | Ru$_{0.3}$CuMo$_{0.3}$Na/LSAA | 320 | 1300 | 7:3 | 2000 | 10.3 | 5.4 | 61.8 |
| 152 | Ru$_{0.3}$CuMo$_{0.3}$Na/LSAA | 330 | 1300 | 1:1 | 2000 | 33.0 | 40.3 | 43.3 |
| 153 | Ru$_{0.3}$CuMo$_{0.3}$Na/LSAA | 340 | 1300 | 7:3 | 2000 | 40.0 | 40.4 | 44.9 |
| 154 | Ru$_{0.3}$CuMo$_{0.3}$Na/LSAA | 330 | 1300 | 1:1 | 2000 | 53.2 | 51.0 | 54.3 |
| 155 | Ru$_{0.3}$CuMo$_{0.3}$Na/LSAA | 340 | 1300 | 1:1 | 2000 | 31.1 | 42.0 | 44.3 |
| 156 | Ru$_{0.6}$Cu$_4$Na$_2$/Mo$_{0.6}$Na$_5$/HS | 320 | 1300 | 1:1 | 2000 | 25.2 | 35.2 | 46.0 |
| 157 | Ru$_{0.6}$Cu$_4$Na$_2$/Mo$_{0.6}$Na$_5$/HS | 320 | 1300 | 3:7 | 2000 | 13.5 | 36.7 | 45.8 |
| 158 | Ru$_{0.6}$Cu$_4$Na$_2$/Mo$_{0.6}$Na$_5$/HS | 330 | 1300 | 1:1 | 2000 | 8.0 | 33.3 | 42.6 |

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. The process for the production of alcohols from CO and H$_2$ comprising contacting said carbon monoxide and hydrogen in the vapor phase at an elevated temperature and pressure for a time sufficient to produce said alcohols with a catalyst of the formula:

$$RuCu_aM_bA_cN_zO_x$$

wherein

A is an alkali metal or an alkaline earth metal or mixture thereof,

M is Mo, W or mixtures thereof, a is about 0.3 to about 10, b is 0.03 to about 5, c is 3 to about 15, z is 0 to about 1 weight percent, and x is the number of oxygen atoms needed to fulfill the valence requirements of the other elements.

2. The process of claim 1 wherein c is about 3 to 10.

3. The process of claim 2 wherein the reaction temperature is between about 250° C.–350° C.

4. The process of claim 3 wherein the contact time of the carbon monoxide and hydrogen with the catalyst is between about 10 to 200 seconds.

5. The process of claim 4 wherein the pressure is at least about 500 psi.

6. The process of claim 5 wherein the reactant gases are fed into the reactor at a space velocity of between about 2000–6000 l/Hr.

7. A method for the production of alcohol from carbon monoxide and hydrogen comprising contacting carbon monoxide and hydrogen in the vapor phase at an elevated temperature and pressure for a time sufficient to produce said alcohol with a catalyst of the formula $$RuCu_aM_bA_cN_zO_x$$

where A is an alkali metal or alkaline earth metal or mixture thereof,

M is Mo, W or mixtures thereof, a is about 0.3 to 10, b is about 0.03 to 5, c is about 0.3 to 15, z is 0 to about 1 weight percent, and x is the number of oxygen atoms needed to fulfill the valence requirements of the other elements, wherein said catalyst is prepared by impregnating a porous support with a solution comprising the metal salts of the catalyst components, drying the impregnated support and partially reducing the catalyst on said support.

8. The method of claim 7 wherein c is about 3 to about 10.

9. The method of claim 8 wherein said support is a low surface area alumina.

10. The method of claim 7 wherein said process further comprises calcining said dried support for about 2 to 5 hours at between 300° to 400° C. prior to reduction.

11. The process of claim 7 wherein said impregnation step further comprises multiple impregnation steps with the same solution.

12. The process of claim 11 wherein said multiple impregnation steps are made with different solutions.

13. The process of claim 12 wherein said solutions contain at least one different catalyst component.

14. The process of claim 11 further comprising drying said support between each impregnation step.

15. The process of claim 13 further comprising drying said support between each impregnation step.

* * * * *